(12) United States Patent
Krueger et al.

(10) Patent No.: US 8,308,813 B2
(45) Date of Patent: Nov. 13, 2012

(54) ANTI-OBESITY DIVERTER STRUCTURE

(75) Inventors: Katie Krueger, Merrimack, NH (US);
Harold M. Martins, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/959,870

(22) Filed: Dec. 3, 2010

(65) Prior Publication Data

US 2011/0137226 A1  Jun. 9, 2011

Related U.S. Application Data

(63) Continuation of application No. 11/443,516, filed on May 30, 2006, now Pat. No. 7,867,283.

(51) Int. Cl.
 *A61F 2/04* (2006.01)
(52) U.S. Cl. .................................. 623/23.65
(58) Field of Classification Search .... 623/23.64–23.65, 623/23.7, 23.68, 2.13, 2.14, 2.16; 600/29–30; 604/8
See application file for complete search history.

(56) References Cited

U.S. PATENT DOCUMENTS

| | | |
|---|---|---|
| 4,315,509 A | 2/1982 | Smit |
| 4,666,442 A | 5/1987 | Arru et al. |
| 5,306,300 A | 4/1994 | Berry |
| 5,653,760 A | 8/1997 | Saffran |
| 5,800,514 A | 9/1998 | Nuñez et al. |
| 5,820,584 A | 10/1998 | Crabb |
| 6,146,389 A | 11/2000 | Geitz |
| 6,379,816 B1 | 4/2002 | De Loose et al. |
| 6,508,833 B2 | 1/2003 | Pavcnik et al. |
| 6,517,575 B1 | 2/2003 | Yang et al. |
| 6,576,005 B1 | 6/2003 | Geitz |
| 6,740,121 B2 | 5/2004 | Geitz |
| 6,755,869 B2 | 6/2004 | Geitz |
| 6,946,002 B2 | 9/2005 | Geitz |
| 7,175,669 B2 | 2/2007 | Geitz |
| 7,220,237 B2 | 5/2007 | Gannoe et al. |
| 7,563,276 B2 | 7/2009 | Osborne et al. |

(Continued)

FOREIGN PATENT DOCUMENTS

EP   1 508 312 A1   2/2005

(Continued)

OTHER PUBLICATIONS

PCT Notification of Transmittal of the International Search Report and the Written Opinion of the International Searching Authority, or the Declaration for the International Application No. PCT/US2007/012258, Nov. 13, 2007 (1 page).

(Continued)

*Primary Examiner* — Melanie Tyson
*Assistant Examiner* — Son Dang
(74) *Attorney, Agent, or Firm* — Fay Kaplun & Marcin, LLP

(57) ABSTRACT

The anti-obesity diverter structure includes a laminate structure having papilla-supplied and pylorus-supplied surfaces. The laminate structure is sized to fit longitudinally within a duodenum such that a transverse clearance is provided between the papilla-supplied surface and papilla of Vater. The laminate structure is secured within the duodenum to define papilla-supplied and pylorus-supplied lumens therein. The papilla-supplied lumen receives the digestive fluid from the papilla of Vater, and provides a conduit for the digestive fluid therein. The pylorus-supplied lumen receives the chyme from the pylorus and provides a conduit for the chyme therein. The laminate structure is impervious or semi-permeable to the chyme and digestive fluid.

7 Claims, 5 Drawing Sheets

U.S. PATENT DOCUMENTS

| | | |
|---|---|---|
| 2001/0039450 A1 | 11/2001 | Pavcnik et al. |
| 2002/0055772 A1 | 5/2002 | McGuckin, Jr. et al. |
| 2003/0040804 A1 | 2/2003 | Stack et al. |
| 2003/0109931 A1 | 6/2003 | Geitz |
| 2003/0181974 A1 | 9/2003 | Xie et al. |
| 2003/0199991 A1 | 10/2003 | Stack et al. |
| 2004/0039452 A1 | 2/2004 | Bessler |
| 2004/0049145 A1* | 3/2004 | Flick ............................... 602/41 |
| 2004/0092892 A1 | 5/2004 | Kagan et al. |
| 2004/0092974 A1 | 5/2004 | Gannoe et al. |
| 2004/0107004 A1 | 6/2004 | Levine et al. |
| 2004/0117031 A1 | 6/2004 | Stack et al. |
| 2004/0138644 A1 | 7/2004 | DiCarlo et al. |
| 2004/0148034 A1 | 7/2004 | Kagan et al. |
| 2004/0220682 A1 | 11/2004 | Levine et al. |
| 2004/0249362 A1 | 12/2004 | Levine et al. |
| 2005/0043817 A1 | 2/2005 | McKenna et al. |
| 2005/0075622 A1 | 4/2005 | Levine et al. |
| 2005/0080395 A1 | 4/2005 | Levine et al. |
| 2005/0125075 A1 | 6/2005 | Meade et al. |
| 2005/0256587 A1 | 11/2005 | Egan |
| 2006/0116752 A1 | 6/2006 | Norton et al. |
| 2007/0156159 A1 | 7/2007 | Gannoe et al. |

FOREIGN PATENT DOCUMENTS

| | | |
|---|---|---|
| WO | 2004049982 A2 | 6/2004 |

OTHER PUBLICATIONS

PCT International Search Report for International Application No. PCT/US2007/012258, Nov. 13, 2007 (6 pages).

PCT Written Opinion of the International Searching Authority for International Application No. PCT/US2007/012258, Nov. 13, 2007 (9 pages).

* cited by examiner

ANTI-OBESITY DIVERTER STRUCTURE

CROSS-REFERENCE TO RELATED APPLICATION

This application is a continuation of U.S. application Ser. No. 11/443,516, filed May 30, 2006, the entire contents of which are incorporated herein by reference.

FIELD OF THE INVENTION

The present invention relates generally to anti-obesity implants and methods for using the same. More specifically, the present invention relates to anti-obesity diverter structures which are secured in the duodenum adjacent to the stomach to reduce digestion and absorption of food.

BACKGROUND OF THE INVENTION

The incidence of obesity and its associated health-related problems has become significant. The causes of obesity involve a complex interplay of genetic, environmental, psycho-behavioral, endocrine, metabolic, cultural, and socioeconomic factors. Severe obesity is frequently associated with significant comorbid medical conditions, including coronary artery disease, hypertension, type II diabetes mellitus, gallstones, nonalcoholic steatohepatitis, pulmonary hypertension, and sleep apnea. Obesity is a leading cause of preventable death in the U.S. The spectrum of comorbid conditions associated with obesity includes cancer, osteoarthritis, and heart disease. The economic cost of obesity is substantial.

Current treatments for obesity range from diet, exercise, behavioral modification, and pharmacotherapy to various types of surgery, with varying risks and efficacy. In general, nonsurgical treatments, although less invasive, achieve only relatively short-term and limited weight loss in most patients. Non-surgical treatments are utilized for patients such as with a body-mass index (BMI) which is greater than 30, and have not proven very effective. Surgical treatments include gastroplasty to restrict the capacity of the stomach to hold large amounts of food, such as by stapling or "gastric banding". Other surgical procedures include gastric bypass and gastric "balloons" which, when deflated, may be inserted into the stomach and then are distended by filling with saline solution.

Surgical interventions may be performed on those patients with a BMI which is greater than 40 (deemed morbidly obese). Surgical interventions may include restrictive operations that reduce the size of the stomach pouch to limit food intake. Surgical interventions may also include malabsorptive procedures that rearrange the small intestine in an attempt to decrease the functional length or efficiency of nutrient absorption, or a combination thereof. One combination procedure is Gastric Bypass (GPB or Roux-en-Y) which has been effective for most patients who maintain about 70% of excess weight loss after 5 years, and 50% thereof after 10 years. Both of these types of procedures may be performed laparoscopically, but may have complications. Also, GPB is normally irreversible. Other treatment approaches are being considered. Excess weight loss is the loss of weight which is greater than the ideal body weight.

The need exists for low cost, less invasive interventions for the treatment of obesity, including morbid obesity.

SUMMARY OF THE INVENTION

The anti-obesity diverter structure of the present invention includes a laminate structure having papilla-supplied and pylorus-supplied surfaces, and proximal and distal ends. The laminate structure has a pair of lateral edges each of which extends between the proximal and distal ends. The lateral edges define a width of the laminate structure. The laminate structure is sized to fit longitudinally within a duodenum such that a transverse clearance is provided between the papilla-supplied surface and a papilla of Vater on an inner surface of the duodenum.

A retainer structure is connected to the laminate structure. The retainer structure secures the laminate structure within the duodenum such that the papilla-supplied surface faces the papilla of Vater. The retainer structure further secures the laminate structure within the duodenum such that the lateral edges engage the inner surface of the duodenum to define papilla-supplied and pylorus-supplied lumens within the duodenum. The papilla-supplied lumen has a periphery which is defined by the papilla-supplied surface and a section of the inner surface of the duodenum which faces said papilla-supplied surface. The pylorus-supplied lumen has a periphery which is defined by the pylorus-supplied surface and a section of the inner surface of the duodenum which faces the pylorus-supplied surface.

The retainer structure further secures the laminate structure within the duodenum such that the papilla-supplied lumen is positioned to receive a digestive fluid from the papilla of Vater. The papilla-supplied lumen provides a conduit for the digestive fluid therein to flow to the distal end. The laminate structure is impervious or semi-permeable to the digestive fluid within the papilla-supplied lumen.

The retainer structure further secures the laminate structure within the duodenum such that the pylorus-supplied lumen is positioned to receive a chyme from a pylorus which leads to the duodenum. Chyme is the partially digested food which flows into the duodenum from the stomach. The pylorus-supplied lumen provides a conduit for the chyme therein to flow to the distal end. The laminate structure is impervious or semi-permeable to the chyme within the pylorus-supplied lumen.

The anti-obesity diverter structure, when secured in the proper location within the duodenum, reduces or prevents mixing of the chyme and digestive fluid within the duodenum. The digestive fluid within the duodenum includes biliary and pancreatic juices which reach the interior of the duodenum by flowing through the papilla of Vater which is contiguous with the inner surface of the duodenum. The digestive fluid is supplied to the papilla of Vater by the bile and pancreatic ducts. The anti-obesity diverter structure reduces or prevents mixing of the chyme and digestive fluid by reducing or preventing the digestive fluid which flows through the papilla of Vater from passing through the laminate structure. Consequently, mixing of the digestive fluid with the chyme in the region of the duodenum which is occupied by the anti-obesity diverter structure is reduced or prevented. This reduces the exposure of the chyme to the digestive fluid which reduces the associated chemical breakdown thereof. This is a result of the laminate structure being semi-permeable or impervious to the chyme. The reduction in the mixing of the chyme and digestive fluid provided by the anti-obesity diverter structure delays the absorption of fat by the duodenum and subsequent portions of the digestive system such as the intestines which effects weight loss in the patient. Further, the reduction in the mixing of the chyme and digestive fluid reduces the caloric intake by the patient. Also, this reduction in the mixing reduces the breakdown of fats because the bile is separated from the chyme over the axial length of the anti-obesity diverter structure. Consequently, the chemical transformation of the chyme by the digestive fluid which is normally required for absorption of the nutrients, fats and other substances in the chyme by the duodenum is reduced.

Additionally, the anti-obesity diverter structure reduces the absorption of the nutrients, fats and other substances in the chyme by the duodenum. This reduced absorption results from the laminate structure being semi-permeable or impervious to the chyme. As a result, the chyme which is contained within the pylorus-supplied lumen is partially or completely prevented from reaching the entire inner surface of the portion of the duodenum in which the anti-obesity diverter structure is located. Consequently, the portion of the duodenum in which the anti-obesity dual stent is located is partially prevented from absorbing the nutrients, fats and other substances in the chyme. Reducing the absorption of the nutrients, fats and other substances by the duodenum reduces the caloric intake by the patient. Also, reducing the absorption of the nutrients, fats and other substances reduces the fat intake by the patient which typically reduces the weight thereof.

The anti-obesity diverter structure does not obstruct the passage and flow of the digestive fluid through the papilla of Vater. The digestive fluid includes biliary secretions which flow through the papilla of Vater. The passage and flow of the digestive fluid through the papilla of Vater is provided by the transverse clearance between the laminate structure and papilla of Vater. This allows flow of the digestive fluid through the papilla of Vater into the papilla-supplied lumen. The anti-obesity diverter structure further provides for the conveyance of the digestive fluid through the papilla-supplied lumen to the distal end of the laminate structure. The passage or flow of the digestive fluid through the papilla of Vater which is not obstructed by the anti-obesity diverter structure is beneficial because obstruction of such passage or flow through the papilla of Vater may be undesirable.

The anti-obesity diverter structure separates the food and chyme, which flows from the stomach into the duodenum, from the digestive fluid which includes bile acids and pancreatic enzymes and which promotes lipid absorption. This separation by the anti-obesity diverter structure is provided at the location thereof in the duodenum which is the beginning of the small intestine. The anti-obesity diverter structure treats obesity using a mal-absorptive method. Separating the food from the digestive fluid may reduce the amount of digestion and, consequently, the amount of weight a person gains from eating a specific quantity of food.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
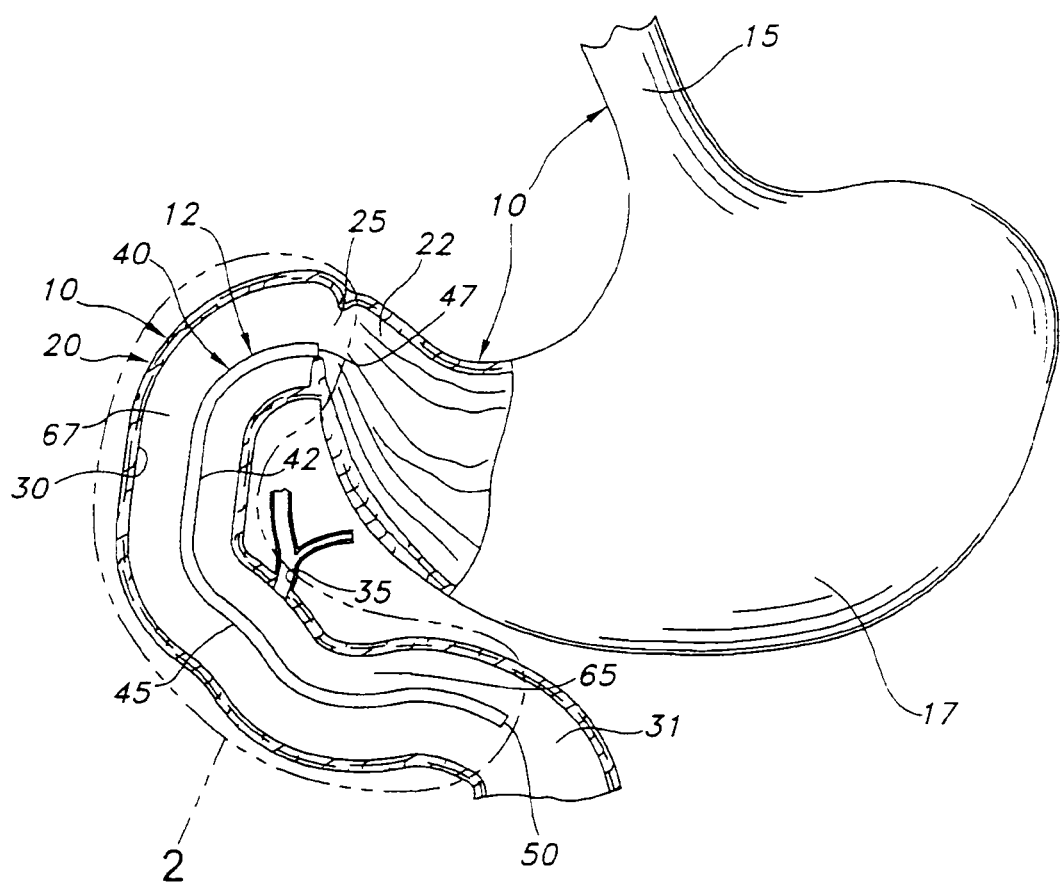
FIG. 1 is an anatomical elevational view of a stomach, duodenum and adjacent portions of the alimentary canal, the wall of the pyloric portion of the stomach and duodenum being broken away to show an anti-obesity diverter structure in accordance with the present invention.

Referring to the drawings and more particularly to FIG. 1, a central portion of the alimentary canal 10 in which the anti-obesity diverter structure 12 is located is illustrated. This portion of the alimentary canal 10 includes the distal segment of the esophagus 15, the stomach 17, and the duodenum 20. The duodenum 20 is the proximate segment of the small intestine. The stomach 17 has a pyloric portion 22 which leads to the duodenum 20 by way of the gastric outlet or pylorus 25. The pylorus 25 forms the distal aperture of the stomach and has an enclosing circular layer of muscle which is normally contracted to close the aperture but which relaxes to provide an open but restrictive passage. Although subject to substantial variation in different individuals, the pylorus 25 has a maximum open diameter of about 2 cm and the duodenum 20 has a diameter which typically is about 18 to 20 mm in a representative patient. The chyme 27 passes from the pyloric portion 22 through the pylorus 25 into the duodenum 20. The duodenum 20 has an inner surface 30 and a lumen 31. The lumen 31 has an outer periphery which is defined by the inner surface 30. The duodenum 20 has a papilla of Vater 32 which is a trumpet-mouthed dilatation of the duodenal wall at the opening of the fused bile and pancreatic ducts. The digestive fluid 37 is supplied through the papilla of Vater 35, and flows into the lumen 31 of the duodenum 20.

The anti-obesity diverter structure 12 is located within the duodenum 20 as shown in FIG. 1. The anti-obesity diverter structure 12 includes a laminate structure 40 which has papilla-supplied and pylorus-supplied surfaces 42, 45. The laminate structure 40 has proximal and distal ends 47, 50. The laminate structure 40 has a pair of lateral edges 52, 55 each of which extends between the proximal and distal ends 47, 50. The lateral edges 52, 55 define a width 57 of the laminate structure 40.

The laminate structure 40 may be formed of expanded polytetrafluoroethylene (ePTFE) or polyurethane. The laminate structure 40 may be formed of biocompatible materials, such as polymers which may include fillers such as metals, carbon fibers, glass fibers or ceramics. Such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the laminate structure 40.

The laminate structure 40 may be formed of materials such as nitinol, Elgiloy, stainless steel, cobalt chromium, including MP35N, cobalt-based alloy, tantalum, niobium, platinum, gold, titanium, combinations thereof and other biocompatible metals, polymers and materials. Additionally, the laminate structure 40 may include structural members which have an inner core formed of tantalum, gold, platinum, iridium, or a combination thereof, and an outer cladding of nitinol to provide composite members for improved radio-opacity or visibility. Examples of such composite members are disclosed in U.S. Patent Application Publication No. 2002/0035396 which is hereby incorporated by reference herein.

The laminate structure 40 may have various embodiments. For example, the laminate structure 40 may be self-expanding or expandable by a balloon. The laminate structure 40 may include one or more coiled stainless steel springs, helically wound coil springs including a heat-sensitive material, or expanding stainless steel structures formed of stainless steel wire in a zig-zag pattern. The laminate structure may be capable of transversely contracting or expanding, such as by transverse or peripheral distension or deformation. Self-expanding laminate structures include structures which mechanically urge the laminate structure to transversely expand, and structures which expand at one or more specific temperatures as a result of the memory properties of the structure material for a specific configuration. Nitinol is a material which may be included in the laminate structure for providing radial expansion thereof both by mechanical urging, or by the memory properties of the nitinol based on one or more specific temperatures. The laminate structures may include one or more of the elements disclosed in U.S. Pat. Nos. 4,503,569, 4,733,665, 4,856,516, 4,580,568, 4,732,152, and 4,886,062 which are hereby incorporated by reference herein. The laminate structure 40 may be a WALLSTENT® RX Biliary Endoprosthesis made by the Boston Scientific Corporation. The laminate structure 40 may be covered by a sleeve structure, such as a PERMALUME® silicone covering which is made by the Boston Scientific Corporation.

The laminate structure 40 may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vasoactive mechanisms.

The laminate structure 40 is sized to fit longitudinally within the lumen 31 of the duodenum 20 such that a transverse clearance 60 is provided between the papilla-supplied surface 42 and papilla of Vater 35. The anti-obesity diverter structure 12 has a retainer structure 62 connected to the laminate structure 40. The retainer structure 62 secures the laminate structure 40 within the lumen 31 such that the papilla-supplied surface 42 faces the papilla of Vater 35.

The retainer structure 62 further secures the laminate structure 40 within the lumen 31 of the duodenum 20 such that the lateral edges 52, 55 engage the inner surface 30 of the duodenum 20. The engagement between the laminate structure 40 and inner surface 30 defines papilla-supplied and pylorus-supplied lumens 65, 67 each of which are contained within the lumen 31.

The papilla-supplied lumen 65 has a periphery which is defined by the papilla-supplied surface 42 and a section of the inner surface 30 of the duodenum 20 which has a facing relation thereto. The pylorus-supplied lumen 67 has a periphery which is defined by the pylorus-supplied surface 45 and a section of the inner surface 30 which has a facing relation thereto.

Figure 3:
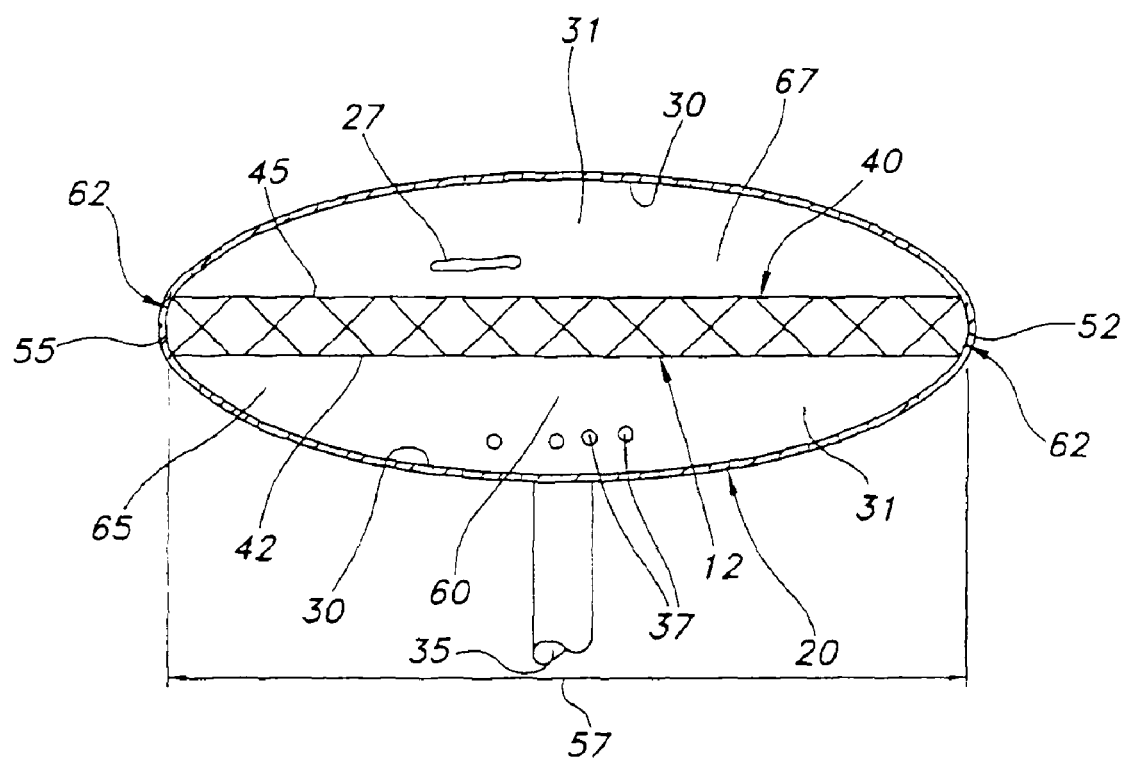
FIG. 3 is a transverse cross sectional view in the plane indicated by line 3-3 of the anti-obesity diverter structure of FIG. 2, the anti-obesity diverter structure being shown as secured within the duodenum.
Figure 4:
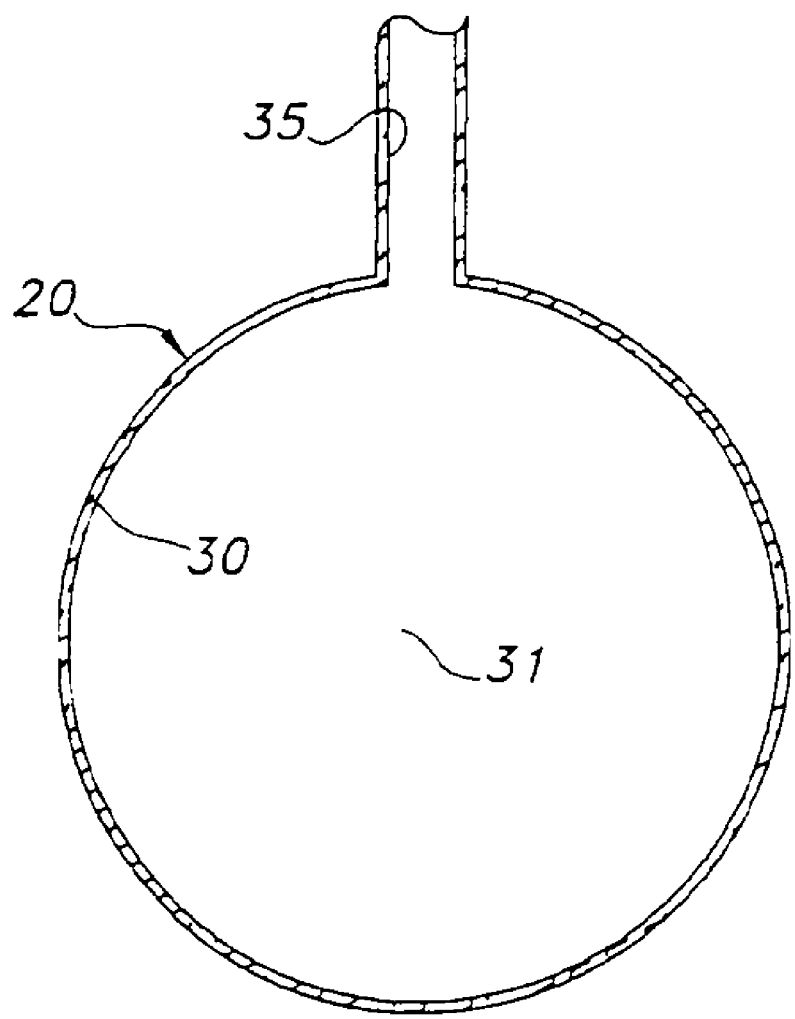
FIG. 4 is a transverse cross sectional view of the duodenum of FIG. 1, the duodenum and papilla of Vater being shown schematically, the duodenum being shown without having the anti-obesity diverter structure therein.

The width 57 of the laminate structure 40 provides for the bisection of the lumen 31 of the duodenum 20 by the laminate structure, as shown in FIG. 3. Consequently, the papilla-supplied and pylorus-supplied lumens 65, 67 have respective cross sections which are substantially the same. The width 57 is sufficiently large such that the cross section of the lumen 31 is substantially elliptical when the laminate structure 40 is secured therein. When the laminate structure 40 is not located in the lumen 31, the cross section thereof is substantially circular, as shown in FIG. 4.

The retainer structure 62 further secures the laminate structure 40 within the lumen 31 of the duodenum 20 such that the papilla-supplied lumen 65 is positioned to receive the digestive fluid 37 from the papilla of Vater 35. The papilla-supplied lumen 65 provides a conduit for the digestive fluid 37 therein to flow to the distal end 50. The digestive fluid 37 exits the papilla-supplied lumen 65 through the distal end 50. The laminate structure 40 is impervious or semi-permeable to the digestive fluid 37 within the papilla-supplied lumen 65.

The retainer structure 62 further secures the laminate structure 40 within the lumen 31 of the duodenum 20 such that the pylorus-supplied lumen 67 is positioned to receive the chyme 27 from the pylorus 25 which leads to the lumen 31. The pylorus-supplied lumen 67 provides a conduit for the chyme 27 therein to flow to the distal end 50. The laminate structure 40 is impervious or semi-permeable to the chyme 27 within the pylorus-supplied lumen 67 which partially or completely prevents the chyme therein from contacting the section of the inner surface 30 which faces the papilla-supplied surface 42. This partially or completely prevents absorption of the chyme 27 and associated nutrients by the section of the inner surface 30 which faces the papilla-supplied surface 42.

Figure 2:
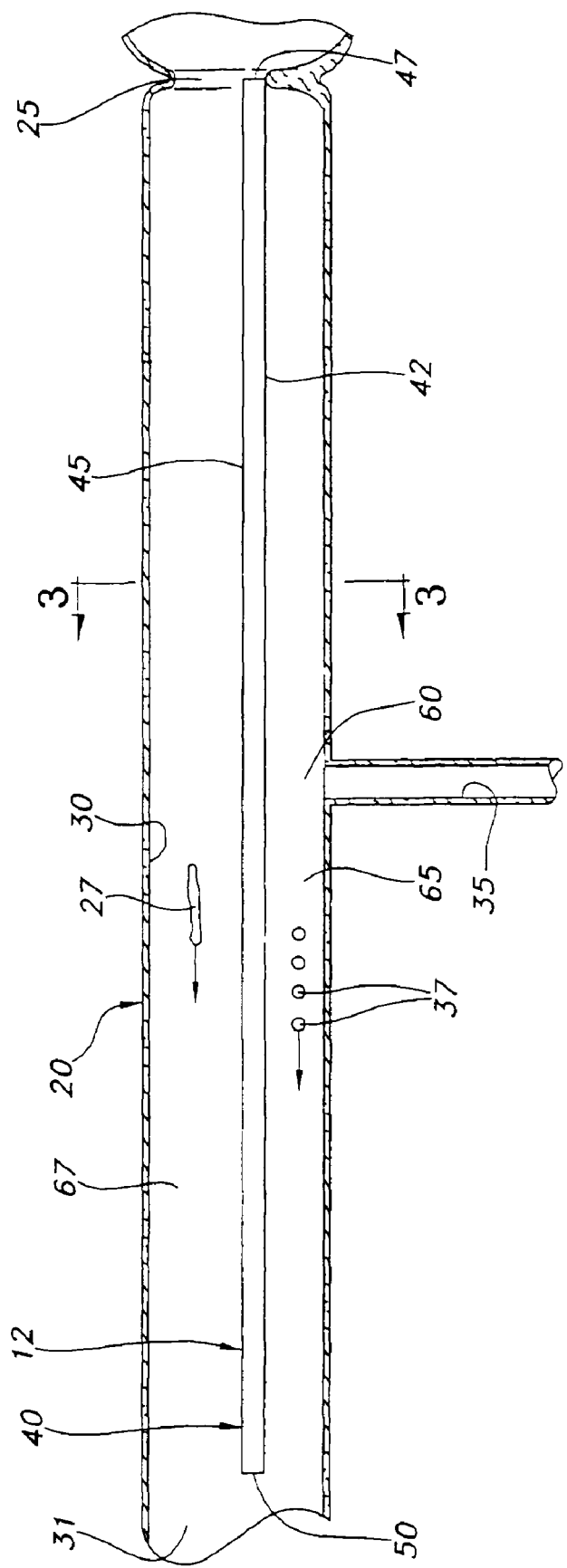
FIG. 2 is an enlarged view of the circled portion 2 of FIG. 1, the anti-obesity diverter structure and duodenum being shown as having substantially straight configurations, the duodenum and papilla of Vater being shown schematically.
Figure 5:
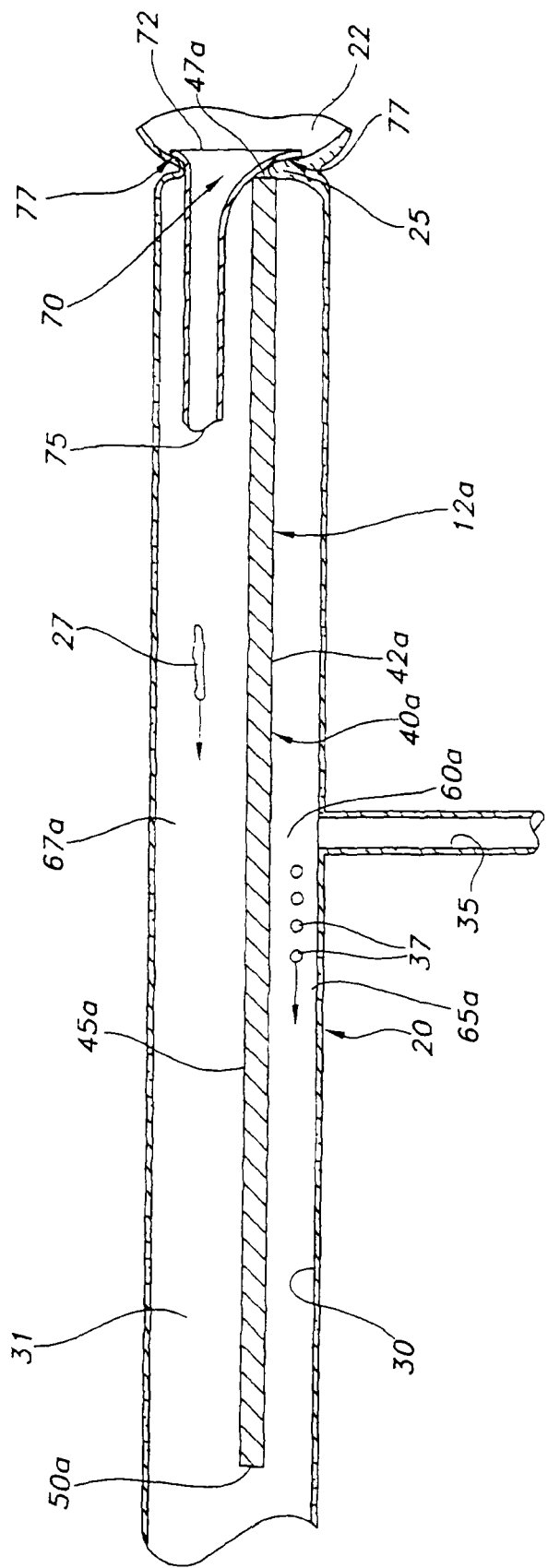
FIG. 5 is a longitudinal cross sectional view which corresponds to FIG. 2 of an alternative embodiment of the anti-obesity diverter structure, the anti-obesity diverter structure being shown as having laminate and funnel structures.

An alternative embodiment of the anti-obesity diverter structure 12a is shown in FIG. 5. Parts illustrated in FIG. 5 which correspond to parts illustrated in FIGS. 1 to 3 have, in FIG. 5, the same reference numeral as in FIGS. 1 to 3 with the addition of the suffix "a". In this alternative embodiment, the proximal and distal ends 47a, 50a define respective laminate proximal and distal ends. The retainer structure 62 defines a laminate retainer structure.

The anti-obesity diverter structure 12a includes a funnel structure 70 which has funnel proximal and distal ends 72, 75. The funnel proximal end 72 has a cross section which is larger than the cross section of the pylorus 25. The funnel distal end 75 has a cross section which is smaller than the cross section of the funnel proximal end 72.

The funnel structure 70 and laminate structure 40a are formed of respective polymer materials. The polymer material included in the funnel structure 70 has a durometer which is smaller than the durometer of the polymer which is included in the laminate structure 40a.

The anti-obesity diverter structure 12a further includes a funnel retainer structure 77 which is connected to the funnel structure 70. The funnel retainer structure 77 secures the funnel structure 70 within the lumen 31 of the duodenum 20 such that the funnel structure extends through the pylorus 25. The funnel proximal end 72 has a proximal position relative to the pylorus 25, and the funnel distal end 75 has a distal position relative thereto.

The relatively small durometer of the polymer material included in the funnel structure 70 provides a substantial flexibility thereof. Consequently, the funnel structure 70 is able to conform to the various sizes of the cross section of the pylorus 25 which correspond, for example, to the opening and closing thereof during digestion. As a result, any interference with the dilation and contraction of the pylorus 25 caused by the funnel structure 70 is insubstantial. The funnel proximal end 72 communicates with the pyloric portion 22, and the funnel distal end 75 communicates with the pylorus-supplied lumen 67a. Consequently, the chyme 27 in the pyloric portion 22 enters the interior of the funnel structure 70 through the funnel proximal end 72. The chyme 27 within the funnel structure 70 exits therefrom through the funnel distal end 75 and flows into the pylorus-supplied lumen 67a.

An anti-obesity diverter structure, such as the anti-obesity diverter structure 12, may be used according to a method for inducing weight loss in a patient. The method includes inserting a laminate structure of the anti-obesity diverter structure into a duodenum, such as the duodenum 20, in a substantially longitudinal relation therewith. An embodiment of the laminate structure to which this inserting may be applied is the laminate structure 40. The laminate structure has papilla-supplied and pylorus-supplied surfaces and proximal and distal ends. The laminate structure has a pair of lateral edges each of which extends between the proximal and distal ends. The lateral edges define a width of the laminate structure.

The method further includes locating the laminate structure within and longitudinally relative to the duodenum such that the proximal end has a proximal position relative to a papilla of Vater, such as the papilla of Vater 35. An embodiment of the proximal end which may be positioned according to this locating is the proximal end 47. The locating further positions the laminate structure such that the distal end has a distal position relative to the papilla of Vater. An embodiment of the distal end which may be positioned according to this locating is the distal end 47.

The locating further positions the laminate structure such that the papilla-supplied surface faces the papilla of Vater. An embodiment of the papilla-supplied surface which may be positioned according to this locating is the papilla-supplied surface 42.

The method further includes engaging a retainer structure of the anti-obesity diverter structure with the inner surface of the duodenum. This engaging secures the laminate structure within the lumen of the duodenum such that the papilla-supplied surface faces the papilla of Vater. An embodiment of the retainer structure to which this engaging may be applied is the retainer structure 62.

The engaging further secures the laminate structure within the lumen of the duodenum such that the lateral edges of the laminate structure engage the inner surface of the duodenum.

The engagement between the laminate structure and inner surface of the duodenum defines papilla-supplied and pylorus-supplied lumens within the lumen of the duodenum. The papilla-supplied lumen has a periphery which is defined by the papilla-supplied surface and a section of the inner surface of the duodenum which faces the papilla-supplied surface. An embodiment of the papilla-supplied lumen which may be provided by the engagement of the laminate structure with the inner surface of the duodenum is the papilla-supplied lumen 65.

The pylorus-supplied lumen has a periphery which is defined by the pylorus-supplied surface and a section of the inner surface of the duodenum which faces the papilla-supplied surface. An embodiment of the papilla-supplied lumen which may be provided by the engagement of the laminate structure with the inner surface of the duodenum is the papilla-supplied lumen 67.

The engaging further secures the laminate structure within the duodenum such that the papilla-supplied lumen is positioned to receive a digestive fluid, such as the digestive fluid 37, from the papilla of Vater. An embodiment of the papilla-supplied lumen which may be positioned to receive the digestive fluid from the papilla of Vater is the papilla-supplied lumen 65.

The engaging further secures the laminate structure within the duodenum such that the pylorus-supplied lumen is positioned to receive a chyme, such as the chyme 27, from a pylorus, such as the pylorus 25, which leads to the duodenum. An embodiment of the pylorus-supplied lumen which may be positioned to receive the chyme from the pylorus is the pylorus-supplied lumen 67.

The entire disclosure of U.S. Pat. No. 6,740,121 is hereby incorporated by reference herein. The entire disclosures of the following U.S. patent applications are hereby incorporated by reference herein:

Title: Anti-Obesity Stent; Inventors: Barry Weitzner, Taryn Deneault, Katie Krueger, Claude Clerc, Harold W. Martins, and William Bertolino; Filed on same date as present U.S. patent application Ser. No. 11/443,537;

Title: Anti-Obesity Dual Stent; Inventors: Katie Krueger, William Bertolino, Barry Weitzner, and Claude Clerc; Filed on same date as present U.S. patent application Ser. No. 11/443,402; and Title: Anti-Obesity Flow Controller; Inventor: Barry Weitzner; Filed on same date as present U.S. patent application Ser. No. 11/443,544.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An anti-obesity device comprising:
an elongated element extending from a proximal end to a distal end and having a width selected to closely match an inner diameter of a portion of a duodenum into which it is to be implanted, the elongated element configured to separate the duodenum into first and second elongated channels after insertion therein, the first channel being positioned so that all chyme flowing through the duodenum enters the first channel and the second channel being positioned so that, when the elongated element is in a desired position with the duodenum, an opening thereto is open to a papilla of vater so that digestive fluids from the papilla of vater enter the second channel, the elongated element being constructed to have a rate of permeability with respect to fluids flowing therepast no greater than a predetermined maximum permeability;

a retainer configured to retain the elongated element at the desired position within the duodenum, a funnel extending from a proximal end having an diameter greater than a diameter of a pylorus to a distal end having an outer diameter smaller than the diameter of the pylorus, wherein the proximal end is configured for insertion at the proximal end of the elongated element to guide the chyme into the first channel; and a funnel retainer configured and dimensioned for insertion proximally of the pylorus and connected to the proximal end of the funnel to retain the funnel in a desired position.

2. The anti-obesity device according to claim 1, wherein the width of the elongated element is selected to bisect the duodenum so that the first and second channels have substantially the same volume.

3. The anti-obesity device according to claim 2, wherein the elongated element is configured and dimensioned to move the duodenum from a biased substantially circular cross-sectional shape to a substantially elliptical cross-sectional.

4. The anti-obesity device according to claim 1, wherein a durometer of the funnel is smaller than a durometer of the elongated element.

5. The anti-obesity device according to claim 1, wherein the elongated element is substantially planar.

6. The anti-obesity device according to claim 1, wherein the maximum rate of permeability is zero.

7. The anti-obesity device according to claim 1, wherein the maximum rate of permeability is selected to allow a partial absorption of chyme by the duodenum.

* * * * *